US00PP22610P3

(12) United States Plant Patent
Page

(10) Patent No.: US PP22,610 P3
(45) Date of Patent: Mar. 27, 2012

(54) ***PELARGONIUM* PLANT NAMED 'VIOLETTY'**

(50) Latin Name: ***Pelargonium* hybrid**
Varietal Denomination: Violetty

(75) Inventor: Stephen Page, Wetering (NL)

(73) Assignee: Walter Blom B.V., Hillegom (NL)

( * ) Notice: Subject to any disclaimer, the term of this patent is extended or adjusted under 35 U.S.C. 154(b) by 248 days.

(21) Appl. No.: 12/583,775

(22) Filed: Aug. 25, 2009

(65) Prior Publication Data

US 2011/0055989 P1 Mar. 3, 2011

(51) Int. Cl.
*A01H 5/00* (2006.01)

(52) U.S. Cl. ..... Plt./324

(58) Field of Classification Search ..... Plt./324
See application file for complete search history.

(56) References Cited

OTHER PUBLICATIONS

UPOV ROM GTITM Computer Database, GTI Jouve Retrieval Software 2010/05 Citation for 'Violetty'.*

* cited by examiner

*Primary Examiner* — Wendy C Haas
(74) *Attorney, Agent, or Firm* — The Webb Law Firm

(57) ABSTRACT

'Violetty' is a new variety of *pelargonium* having a trailing growth habit and numerous tri-colored flowers.

3 Drawing Sheets

Botanical classification: *Pelargonium* hybrid.
Varietal denomination: 'Violetty'.

BACKGROUND OF THE INVENTION

The present invention comprises a new and distinct cultivar of *Pelargonium* hybrid known by the varietal name 'Violetty'. The new variety was discovered in Hillegom, The Netherlands in April of 2005. The new variety is a result of a planned breeding program and is the result of a cross between an unnamed and unpatented *Pelargonium ovale* variety (female parent) and *Pelargonium* 'Splendide' (male parent, unpatented). The purpose of the breeding program was to develop color breaks in the 'Splendide' variety. The new variety has a similar flower color and flower size to its female parent, but differs from its female parent in growth habit. The new variety exhibits a similar growth habit, flower form and foliage shape to its male parent, but differs in flower size from its male parent. 'Violetty' exhibits smaller foliage that is more grayish-green in color than 'Splendide'. Also, 'Violetty' displays a soft pink flower color on its lower petals, compared to white with 'Splendide'. Finally, the growth habit of 'Violetty' is more prostrate with longer trailing or hanging branches than 'Splendide'. The new variety was first asexually reproduced by apical cuttings and tissue culture in July of 2005 in Hillegom, The Netherlands. The new variety has been trial and field tested and has been found to retain its distinctive characteristics and remain true to type through successive propagations.

The following traits have been repeatedly observed and are determined to be unique characteristics of 'Violetty'. Characteristics that distinguish 'Violetty' as a new and distinct cultivar from others known to the breeder include:

1) Free flowering with thousands of flowers produced per plant;
2) Flower color, distinct soft pink color on lower three petals; and 3) Growth habit, 'Violetty' plants have long trailing branches that form dense mats of foliage.

DESCRIPTION OF THE DRAWINGS

The accompanying photographic drawings illustrate the new variety, with the color being as nearly true as is possible with color illustrations of this type.

DESCRIPTION OF THE PLANT

Figure 1:
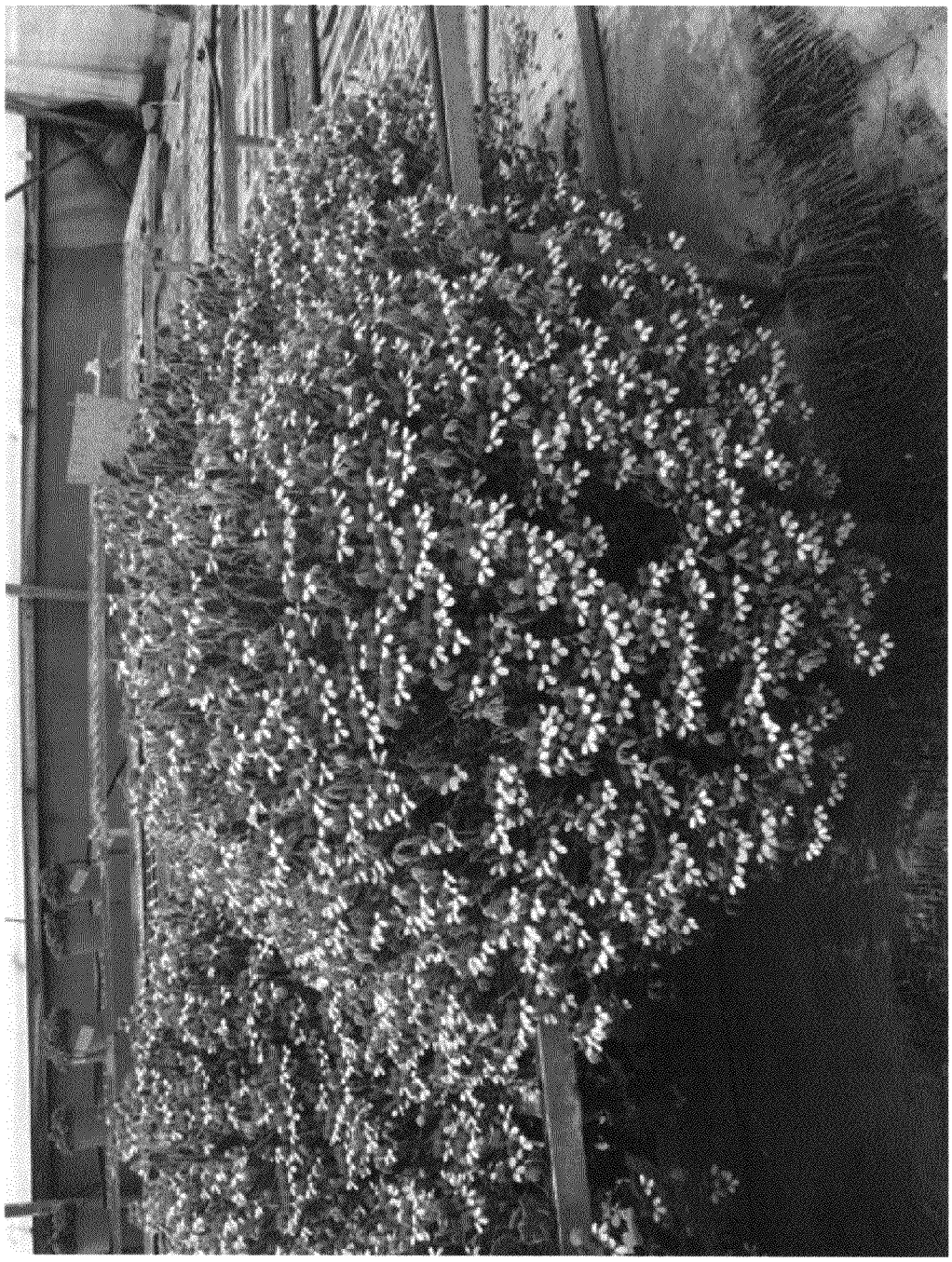
FIG. 1 shows an entire flowering plant of the new variety.
Figure 2:
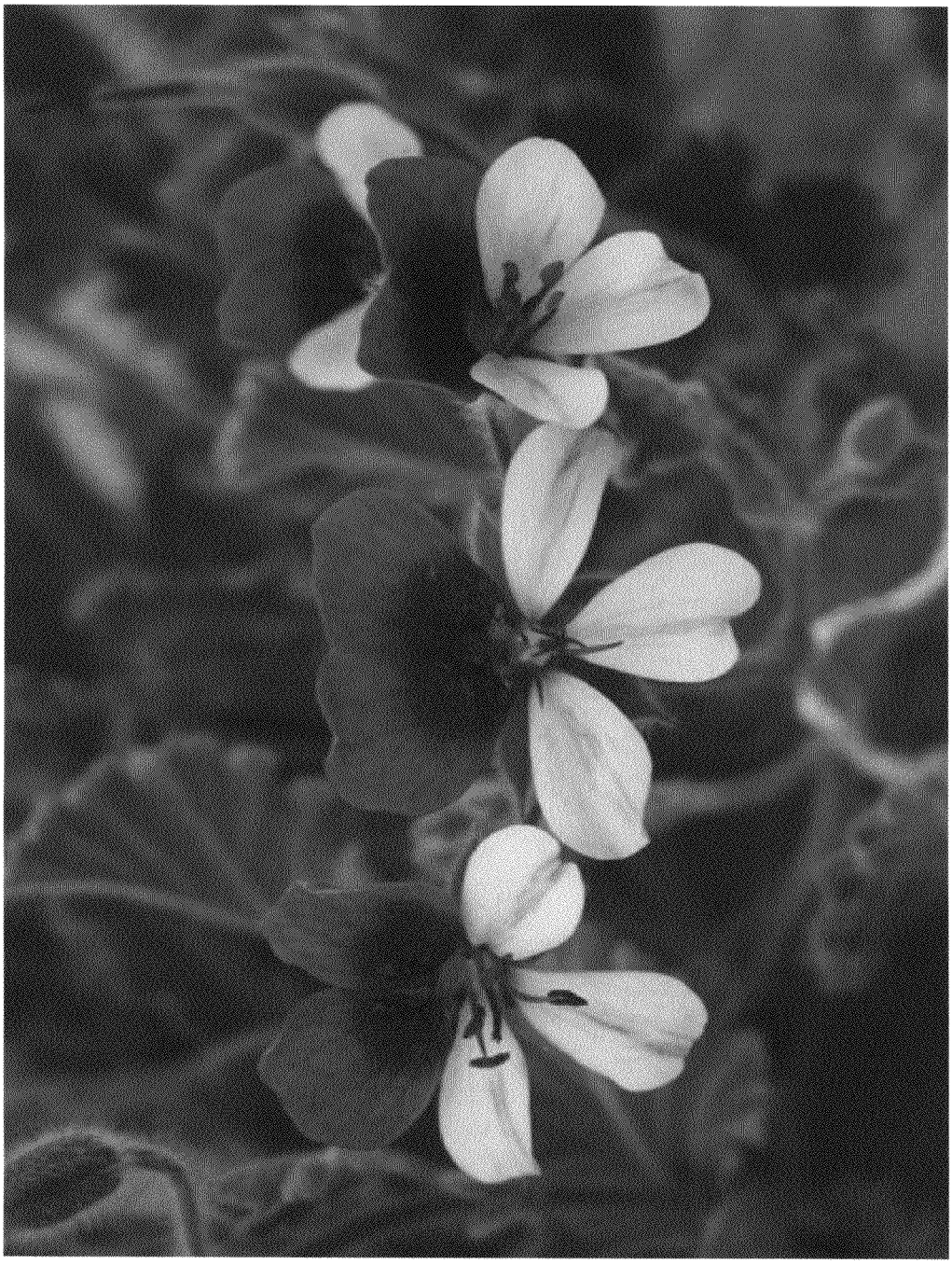
FIG. 2 is a close-up photograph of the petals of the new variety.
Figure 3:
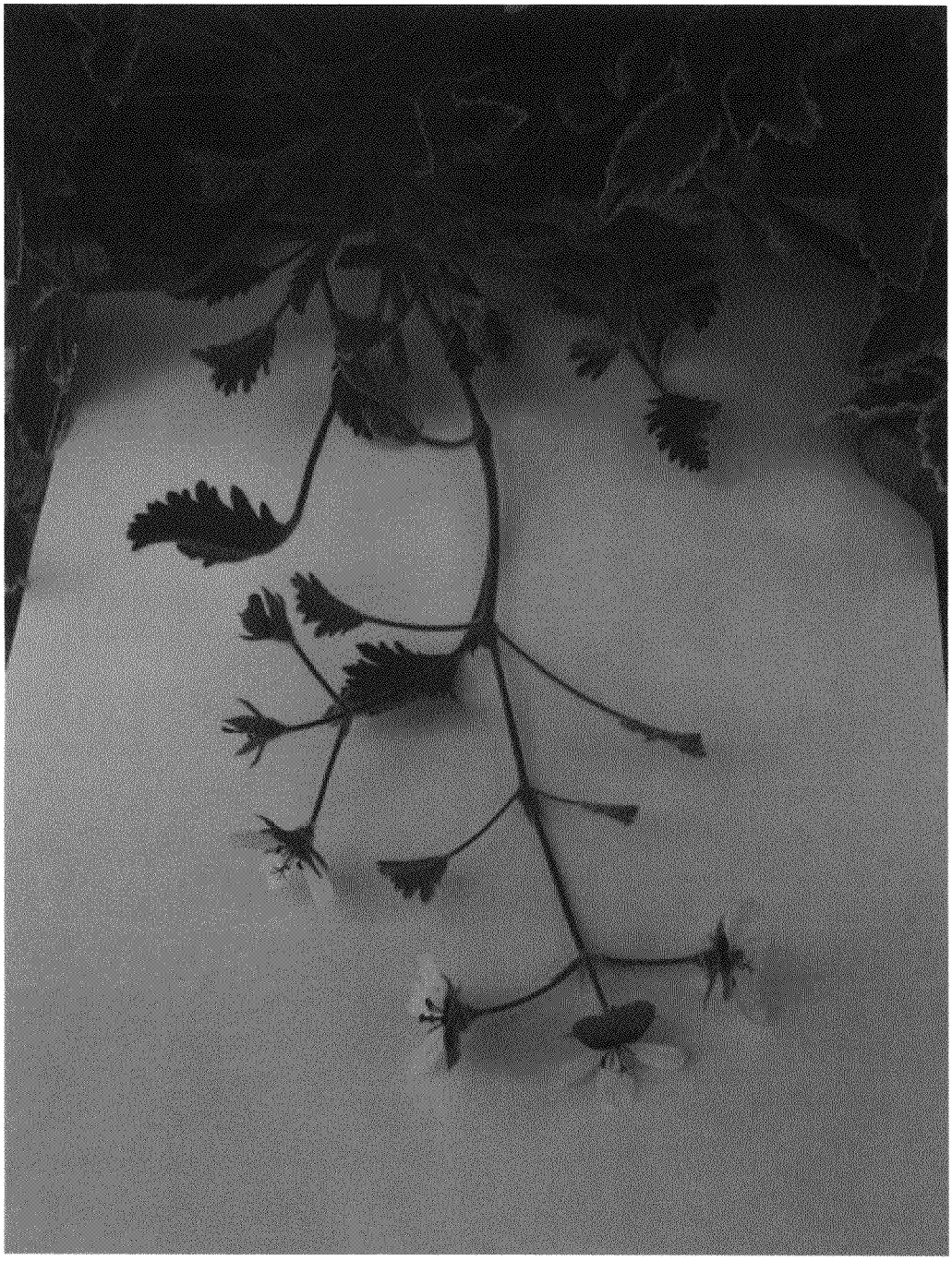
FIG. 3 is a close-up photograph of the leaves and stems of the new variety.

The following detailed description sets forth the characteristics of the new cultivar. The data which defines these characteristics were collected by asexual reproductions carried out in Hillegom, The Netherlands. The color readings were taken under natural light. The new variety was fifteen months old when described and in a 12 cm. container. Color references are primarily to The 1995 R.H.S. Colour Chart of The Royal Horticultural Society of London.

PLANT

Time to initiate roots: About 6-9 days at about 24° C.
Time to develop roots: About 10 days at about 18-25° C.
Time to produce a finished flowering plant from a rooted cutting: About 14-15 weeks in a 12 cm. container.
Form: Plants make a spreading, symmetrical mound.
Height from media surface to top of foliage: Average of 20 cm.
Height from media surface to top of flowers: Average of 28 cm.
Strength (need for artificial support): Plants are prostrate and spreading, no support is required.

Branching habit: Medium branching; plants need pinching to encourage branching.
Plant diameter: 45 cm.
Vigor: Good, but growth of the plants is controlled.
Stem:
*Main stem length.*—Average of 22 cm.
*Diameter.*—Average of 4 mm.
*Color.*—Medium green.
*Texture.*—Soft and hairy.
*Pubescence.*—Soft, short hair is present in a moderate amount.
*Internode length.*—Between 3-5 cm.
Lateral branches:
*Length.*—Average of 10.5 cm.
*Diameter.*—Average of 2 mm.
*Internode length.*—Average of 4.2 cm.
*Texture.*—Hairy.
*Pubescence.*—Soft, short hairs present.
*Color.*—137B.
Foliage:
*Arrangement.*—Alternate.
*Stipules.*—Size: 0.5 cm. Color: Greenish-brown.
*Zone.*—Not present.
*Size of leaf.*—Length: Average of 3.5 cm. Width: Average of 1.8 cm.
*Shape of leaf (generally).*—Petiolated; elliptic.
*Shape of apex.*—Obtuse.
*Shape of base.*—Cuneate.
*Texture.*—Moderate pubescence.
*Aspect.*—Held upright, more or less at right angles to the ground.
*Margin type.*—Serrate (wavy edges).
*Pubescence.*—Upper surface: Light. Lower surface: Medium.
*Color.*—Young leaves: Upper surface: 137D. Lower surface: 138B. Mature leaves: Upper surface: 137B. Lower surface: 138D.
*Petiole.*—Length: Up to 8 cm. Diameter: 1.6-2 mm. Color: 137D, fading to 137C.
*Veins.*—Venation type: Reticulate. Color: Upper surface: 137C. Lower surface: 137D.

INFLORESCENCE

Bud:
*Stage of development when bud characteristics determined.*—At flowering.
*Shape of cluster.*—Pseudoumbel.
*Diameter of cluster.*—5-6 cm.
*Number of buds per cluster.*—3.
*Shape of individual bud.*—Conical.
*Length of individual bud.*—0.8-1.2 cm.
*Width of individual bud.*—0.3-0.8 cm.
Natural flowering season: From March until mid-June in The Netherlands.
Blooming habit: Continuous.
Umbel diameter: Average of 3.5 cm.
Umbel depth: Average of 2.8 cm.
Borne: Umbel, flowers on pedicel, pedicel on peduncle.
Inflorescence position: Above foliage.
Number of inflorescences per lateral branch: Two to four.
Lastingness of an individual flower: One week.
Florets:
*Form.*—Slightly cupped; saucer-shaped.
*Number per umbel.*—3.
*Diameter.*—2-2.2 cm.
*Depth.*—1-1.3 cm.
Petals:
*Overall description.*—There are five petals per inflorescence. The two upper petals are deep red in color with violet shading and a dark violet base. The three lower petals are smaller than the upper petals. The lower petals are pinkish-rose during anthesis.
*Color.*—Upper petals: Upper surface: 46A at the top half of the petal, fading to 53A at the bottom half of the petal. Lower surface: 60A. Lower petals: Upper surface: 69B. Lower surface: 69C.
*Shape.*—Elliptic with a narrower lower part.
*Length.*—1-1.2 cm.
*Width:* 0.5-1 cm.
*Apex shape.*—Oval.
*Margin.*—Smooth; entire.
*Number per floret.*—5.
*Texture.*—Soft and silky.
*Tonality from a distance.*—Red and light pink.
Sepals:
*Quantity.*—5.
*Shape.*—Lanceolate.
*Color.*—Green to light green.
*Length.*—1 cm.
*Width.*—0.3-0.5 cm.
Pedicel:
*Length.*—2-3 cm.
*Diameter.*—1.5 mm.
*Color.*—Brown.
*Texture.*—Pubescence present.
Peduncle:
*Length.*—4-6 cm.
*Diameter.*—1.5-2 cm.
*Texture.*—Slightly pubescent.
*Color.*—Green.
Fragrance: None present.
Disease resistance: No susceptibility to any particular disease observed to date.
Temperature tolerance: Good, will tolerate from −2° C. to +35° C.
Drought tolerance: Good, will tolerate dry conditions.

REPRODUCTIVE ORGANS

Stamens:
*Number (per flower).*—5.
*Filament.*—Length: 1.5-2 mm. Color: Reddish-purple.
*Anthers.*—Shape: Elongated. Length: 0.3-0.5 mm. Color: Reddish-crimson.
*Pollen.*—Color: Yellow. Amount (generally): Plentiful.
Pistils:
*Number.*—1.
*Length.*—2-2.5 mm.
*Style.*—Length: 1 cm. Color: 46B.
*Stigma.*—Shape: 5 parted. Color: 60B. Size: 1-1.5 mm.

I claim:

1. A new and distinct variety of *pelargonium* plant named 'Violetty' as is herein described and illustrated.

* * * * *